(12) United States Patent
Nijkerk et al.

(10) Patent No.: US 7,732,762 B2
(45) Date of Patent: Jun. 8, 2010

(54) METHOD OF INSPECTING A SPECIMEN SURFACE, APPARATUS AND USE OF FLUORESCENT MATERIAL

(75) Inventors: Michiel David Nijkerk, Amsterdam (NL); Pieter Kruit, Delft (NL)

(73) Assignee: Nederlandse Organisatie Voor Toegepast-Natuurwetenschappelijk Onderzoek TNO, Delft VK (NL)

( * ) Notice: Subject to any disclaimer, the term of this patent is extended or adjusted under 35 U.S.C. 154(b) by 427 days.

(21) Appl. No.: 11/572,398

(22) PCT Filed: Jul. 21, 2005

(86) PCT No.: PCT/NL2005/000529

§ 371 (c)(1),
(2), (4) Date: Apr. 17, 2007

(87) PCT Pub. No.: WO2006/009444

PCT Pub. Date: Jan. 26, 2006

(65) Prior Publication Data

US 2007/0272856 A1    Nov. 29, 2007

(30) Foreign Application Priority Data

Jul. 23, 2004  (EP) .................................. 04077130

(51) Int. Cl.
*G01N 23/00* (2006.01)
(52) U.S. Cl. .................. 250/310; 250/306; 250/307; 250/311; 250/397; 250/361 R; 250/362; 250/367; 250/368; 250/369
(58) Field of Classification Search .................. 250/306, 250/307, 310, 311, 397, 361 R, 362, 367, 250/368, 369
See application file for complete search history.

(56) References Cited

U.S. PATENT DOCUMENTS

| | | | | | |
|---|---|---|---|---|---|
| 4,893,009 | A | * | 1/1990 | Kuroda | ........................ 250/310 |
| 5,043,583 | A | * | 8/1991 | Robinson | ..................... 250/397 |
| 6,465,783 | B1 | * | 10/2002 | Nakasuji | ...................... 250/311 |

(Continued)

FOREIGN PATENT DOCUMENTS

EP       1271605       1/2003

(Continued)

OTHER PUBLICATIONS

Ebara Corp. et al, Electron Beam System and Semiconductor Device Manufacturing Method Using the Same, Patent Abstracts of Japan, Publication No. 2003 077413 A, Publication Date Mar. 14, 2003.

(Continued)

*Primary Examiner*—David A Vanore
*Assistant Examiner*—Michael Maskell
(74) *Attorney, Agent, or Firm*—Martin Fleit; Paul D. Bianco; Fleit Gibbons Gutman Bongini & Bianco PL

(57) ABSTRACT

The invention relates to a method of inspecting a specimen surface. The method comprises the steps of generating a plurality of primary beams directed towards the specimen surface, focussing the plurality of primary beams onto respective loci on the specimen surface, collecting a plurality of secondary beams of charged particles originating from the specimen surface upon incidence of the primary beams, converting at least one of the collected secondary beams into an optical beam, and detecting the optical beam.

47 Claims, 9 Drawing Sheets

U.S. PATENT DOCUMENTS

| | | | |
|---|---|---|---|
| 6,797,954 B2 * | 9/2004 | Shinada et al. | 850/10 |
| 6,844,550 B1 * | 1/2005 | Yin et al. | 850/9 |
| 6,888,139 B2 * | 5/2005 | Tsuneta et al. | 250/311 |
| 6,979,823 B2 * | 12/2005 | Shinada et al. | 850/6 |
| 7,244,949 B2 * | 7/2007 | Knippelmeyer et al. | 250/396 ML |
| 7,262,418 B2 * | 8/2007 | Lo et al. | 250/396 R |
| 2002/0171030 A1 * | 11/2002 | Howells | 250/201.3 |
| 2003/0164460 A1 * | 9/2003 | Shinada et al. | 250/492.3 |
| 2004/0245465 A1 * | 12/2004 | Steigerwald et al. | 250/310 |
| 2005/0045821 A1 | 3/2005 | Noji et al. | |
| 2005/0121611 A1 | 6/2005 | Kimba et al. | |
| 2006/0016989 A1 * | 1/2006 | Nakasuji et al. | 250/310 |
| 2006/0249686 A1 * | 11/2006 | Slowko | 250/397 |
| 2008/0068123 A1 * | 3/2008 | Aksyuk et al. | 337/363 |
| 2008/0308729 A1 * | 12/2008 | Kimba et al. | 250/307 |

FOREIGN PATENT DOCUMENTS

| | | |
|---|---|---|
| JP | 63-175325 | 7/1988 |
| JP | 2003-77413 | 3/2003 |
| JP | 2003077413 A * | 3/2003 |
| WO | WO 2006/009444 | 1/2006 |

OTHER PUBLICATIONS

H. Niedrig et. al., Information depth and spatial resolution in BSE microtomography in SEM, Nuclear Instruments and Methods in Physics Research, Section—B: Beam Interactions with Materials and Atoms, vol. 142, No. 4, Aug. 1, 1998, pp. 523-534, XP004141580, ISSN: 0168-583X, Elsevier Science B.V.

Hitoshi Sunaoshi et al., In-Situ beam position monitoring system for electron beam lithography,SPIE, vol. 3777, Jul. 1999, pp. 15-22, XP002306788, Part of the SPIE Conference on Charged Particle Options IV, Denver, Colorado.

Jeol Ltd. et al, Charged Particle Detecting Device, Patent Abstracts of Japan, Publication No. 63 175325 A, Publication Date Jul. 19, 1988.

* cited by examiner

METHOD OF INSPECTING A SPECIMEN SURFACE, APPARATUS AND USE OF FLUORESCENT MATERIAL

The invention relates to a method of inspecting a specimen surface, comprising the steps of generating a plurality of primary beams directed towards the specimen surface, focussing the plurality of primary beams onto respective loci on the specimen surface, and collecting a plurality of secondary beams of charged particles originating from the specimen surface upon incidence of the primary beams.

Such a method is known from e.g. patent publication U.S. Pat. No. 6,465,783, disclosing methods and apparatus for inspecting semi-conductor wafers and other types of specimens, such as masks, using parallel charged particle beams, e.g. electron beams. An emitter array, including a plurality of charged-particle-beam emitters produces a plurality of primary beams that propagate along a substantially parallel direction. The primary beams pass simultaneously through projection lenses so as to cause the beams to be focused onto respective loci on the surface of the specimen so as to cause each locus to emit backscattered and/or secondary electrons, i.e. electrons generated by a secondary process. The backscattered and/or secondary electrons are collected and detected by a secondary-electron array including multiple detector units. Each detector unit collects and detects secondary electrons emitted from a respective locus to obtain information from the surface of the semi-conductor wafer or other type of specimen.

During manufacture of integrated circuits it is necessary to inspect at various stages the substrate for defects. Inspection tools are indispensable for improving the yield in the semiconductor manufacturing process. The requirements of inspection machines are prescribed in international recognized documents which dictate ever increasing sensitivities for future years.

A well-known inspection method which in practice does not suffer the resolution limit of optical microscopy is an inspection technique using a scanning electron beam to inspect wafers created in the semiconductor industry. In conventional electron beam inspection machines, a raster scan over the sample is performed with a single focussed electron probe. On irradiation with an electron probe, the substrate emits backscattered electrons and secondary electrons, from the point of incidence that can subsequently be detected with an electron detector, and the presence of any defects can be determined from the resulting pattern of backscattered or secondary electrons. The electron detector typically comprises a scintillator which collects electrons, a light guide for guiding photons, and a photon detector.

The resolution capability of such a single electron beam system exceeds that of optical techniques, yet the long scanning time per wafer results in a very low throughput. Higher productivity can only be obtained by increasing the current because faster scanning while maintaining the same current leads to prohibitive decrease in signal-to-noise ratio. However, an increase of current occurs at the cost of resolution since Coulomb interactions (mutual repulsion of electrons) in the electron beam increase the minimum possible probe size. Hence, the amount of current in a scanning probe may be limited, thus reducing the scanning speed of the electron beam system to undesired values.

Consequently, a technique with a single electron beam is impractical for production level inspection in the semiconductor industry. Instead, it is used for supplementary defect inspection of single defects that must be inspected at higher resolution.

From the condition that a minimum signal-to-noise ratio is required it can be seen that the productivity of an inspection technique is proportional to the current that can be detected while maintaining resolution. The productivity of a single beam inspection machine can thus be increased by using multiple electron beams in parallel, as disclosed in e.g. patent publication U.S. Pat. No. 6,465,783. Simply put, a machine with ten beams increases the productivity ten-fold and so on. Regardless of practical difficulties, the productivity of a multi beam system is highest if the footprint of the substrate (say a 300 mm wafer) is filled with as many individual beams as possible. For a practical system, the inspection field should be significantly smaller than 300 mm. A smaller field gives the possibility to use the full productivity enhancement over a small region of the wafer, for instance a single die. A larger field leads to the unwanted side effect that some of the beams are not used in the inspection process efficiency. Thus, when choosing between two different multi-beam systems with an equal number of beams, the one with the smaller footprint is the preferred system. For such systems it is crucial that each beam has its own electron detector in such a manner that cross talk between the various detectors can be neglected. One of the factors limiting the multiplicity are the dimensions of the electron detectors and the electrical means to transport the electronic information which is contained in the secondary electron beams, especially in the case of a multitude of primary beams.

It is an object of the invention to provide a method according to the preamble, whereby the disadvantages identified above are reduced. In particular, the invention aims at obtaining a method of inspecting a specimen surface, wherein the multiplicity limitation is reduced.

According to a first aspect of the present invention, there is provided a method of inspecting a specimen surface, comprising the steps of generating a plurality of primary beams directed towards the specimen surface, focussing the plurality of primary beams onto respective loci on the specimen surface, collecting a plurality of secondary beams of charged particles originating from the specimen surface upon incidence of the primary beams, converting at least one of the collected secondary beams into an optical beam, and detecting the optical beam.

By converting at least one of the collected secondary beams into an optical beam, and by detecting the optical beam, it is not longer necessary to detect the secondary beam at a location near the surface of the specimen where interference of the secondary beams is minimal. Since the characteristics of the optical beam can also be determined at another location, more space is available for retrieving the information which is originally present in the secondary beam, so that more freedom with respect to the detection system, inclusive data transport means, is obtained. On the other hand, the information which is carried by the secondary particle beam may be detected more compactly. As a consequence, the plurality of primary beams can be arranged closer to each other, thereby reducing the multiplicity limitations of the conventional inspecting method and enhancing the productivity of the inspection apparatus.

It is noted that in the context of this application a specimen surface encompasses the top layer of the specimen including material just below the boundary plane of the specimen.

It is further noted that that the optical beam resulting from the converting step in the method according to the invention propagates at least initially in a non-waveguiding volume or region. The non-waveguiding volume may include a structure. The non-waveguiding volume may include a free space.

According to a preferred embodiment of the invention, the detecting step includes detecting the optical beam with an optical detector, and the converting step includes converting at least one of the collected secondary beams at a plane into the optical beam, the optical beam being imaged through free space, wherein the optical beam traverses at least one of the primary beams, onto a plane in which the optical detector is located. In this way, the primary beams are converted into optical signals and the plane where the optical signals are generated is imaged through free space, not hindering the primary beams, on a plane with the optical detectors. Further, the primary beams can be located closer together, thus increasing the productivity, without the detectors having to be more closely positioned with respect to one another in the limited space available.

In a preferred embodiment according to the invention, the step of converting the collected secondary beam into the optical beam is accomplished by means of fluorescent material. Advantageously, the fluorescent material does not impose requirements with respect to a minimum distance between the individual primary beams. Thus, the distance between the primary beams can be minimized. Further, the converting step can be achieved in a relatively cheap manner. In a yet further embodiment, the fluorescent material is disposed between an emitter of the plurality of primary beams and the specimen surface, wherein the fluorescent material is arranged to allow the primary beams to pass. In this way, the usage of space within the inspection apparatus is improved. In a further embodiment, a micro channel plate (MCP) is arranged to allow the primary beams to pass, wherein the micro channel plate is disposed between the specimen and the converting means. In this way, the current in the secondary beam is increased, thus increasing the signal in the optical beam. In further preferred embodiment of the invention, the step of detecting the optical beam is accomplished in a detection region outside of a volume enclosing the space being traversed by the plurality of primary beams. In this way, advantage is taken from the fact that the optical beam can pass the primary beams without substantial interference, so that the optical beam can be detected in a region that is not restricted by conditions determined by the geometry of the primary beams. As a consequence, the primary beams can be positioned even closer to each other, resulting in an even faster inspecting method and apparatus.

It is noted that in the above-mentioned embodiment also the problem is reduced of designing the data transport system from the detection means to means for further processing and interpreting means. Due to the desired scanning speed of the inspecting apparatus, high speed data connection means may be required, such as coaxial cables, which in a conventional multi beam apparatus can limit a minimum distance between individual beams. By detecting the optical beams in a detection region outside of the volume enclosed by the space being traversed by the plurality of primary beams, designing parameters with respect to the high speed data connection are relaxed, thus allowing an ever smaller distance between the individual primary beams.

By focussing the optical beam onto a detection system in the detection region, e.g. by means of a lens system, the detection of the optical beam can be carried out more accurately, thereby improving the performance of the inspecting method and apparatus.

According to a second aspect of the present invention, there is provided an apparatus for inspecting a specimen surface, comprising at least one emitter arranged to emit a plurality of primary beams directed towards the specimen surface, focussing means arranged to focus the plurality of primary beams onto respective loci on the specimen surface, collecting means for collecting a plurality of secondary beams of charged particles originating from the specimen surface upon incidence of the primary beams, converting means for converting at least one of the collected secondary beams into an optical beam, and detection means for detecting the optical beam.

According to a third aspect of the present invention, there is provided a use of fluorescent material in the method of inspecting a specimen surface according to claim 1 for converting the collected beam of secondary particles into the optical beam.

According to a fourth aspect of the present invention, there is provided a method of inspecting a specimen surface, comprising the steps of generating a plurality of primary beams directed towards the specimen surface, focussing the plurality of primary beams onto respective loci on the specimen surface, collecting a plurality of secondary beams of charged particles originating from the specimen surface upon incidence of the primary beams, and converting at least one of the collected secondary beams directly into an electronic signal According to a fifth aspect of the present invention, there is provided an apparatus for inspecting a specimen surface, comprising at least one emitter arranged to emit a plurality of primary beams directed towards the specimen surface, focussing means arranged to focus the plurality of primary beams onto respective loci on the specimen surface, collecting means for collecting a plurality of secondary beams of charged particles originating from the specimen surface upon incidence of the primary beams, and converting means for converting at least one of the collected secondary beams directly into an electronic signal.

According to a sixth aspect of the invention, there is provided a method of inspecting a specimen surface, comprising the steps of generating one or more primary beams directed towards the specimen surface;

collecting one or more secondary beams of charged particles originating from the specimen surface upon incidence of one or more primary beams;

converting at least one of the collected secondary beams into an optical beam;

directing the optical beam to a detector, and detecting the optical beam.

According to a seventh aspect of the present invention, there is provided an apparatus for inspecting a specimen surface, comprising:

one or more emitters arranged to emit one or more primary beams directed towards the specimen surface;

collecting means for collecting one or more secondary beams of charged particles originating from the specimen surface upon incidence of the one or more primary beams;

converting means for converting at least one of the collected secondary beams into an optical beam;

directing means for directing the optical beam towards a detection means, and the detection means for detecting the optical beam.

According to an eighth aspect of the present invention, there is provided a fluorescent plate for use in an inspection apparatus according to any of preceding claims 33-54.

According to a ninth aspect of the present invention, there is provided a fluorescent plate and a directing means for use in an inspection apparatus according to any of preceding claims 33-54.

According to a tenth aspect of the present invention, there is provided a use of a micro channel plate (MCP) disposed between a specimen surface and a converting means for converting a primary beam to a converted beam having a signal constructed such that the primary beam is allowed to pass the micro channel plate, to increase the signal in the converted beam.

Other advantageous embodiments according to the invention are described in the following claims.

By way of example only, embodiments of the present invention will now be described with reference to the accompanying figures in which FIG. 1 shows a schematic view of an apparatus according to a first embodiment of the invention;

Figure 5:
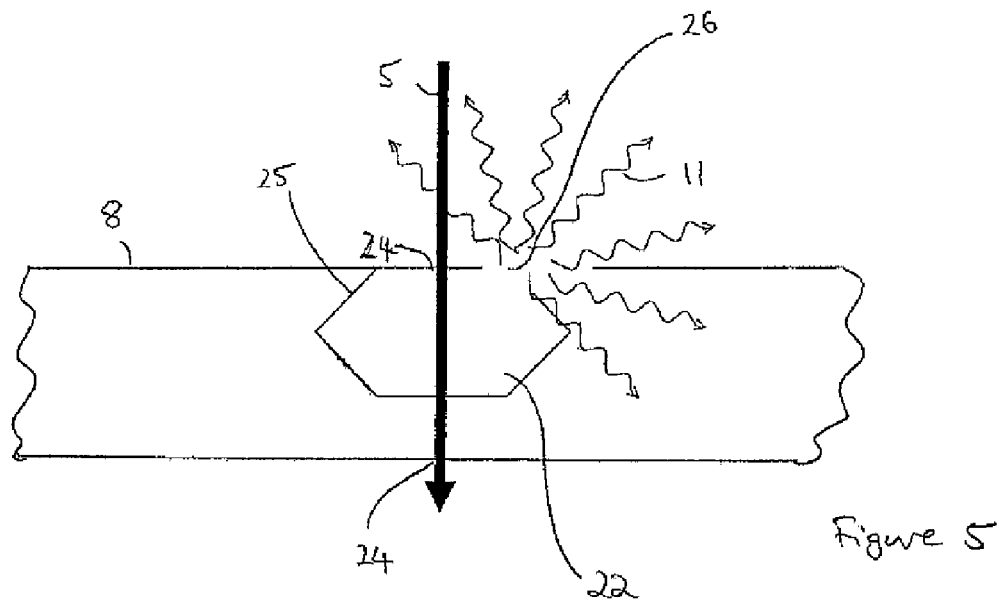
Figure 6:
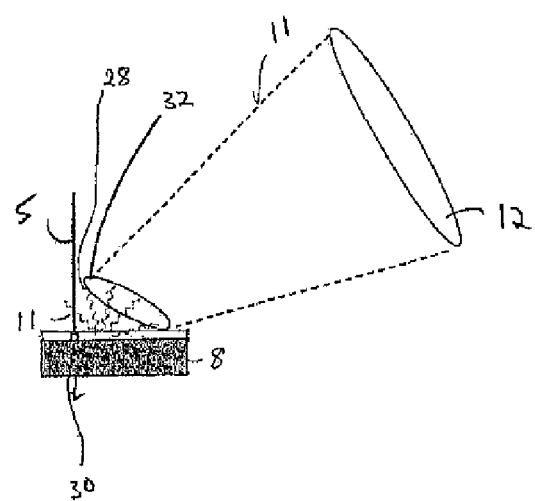
Figure 7:
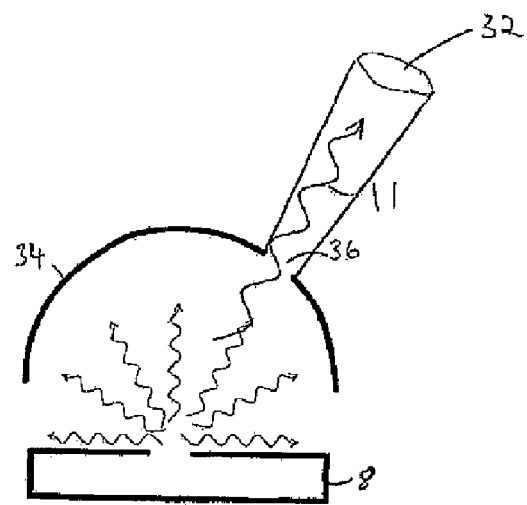
Figure 8:
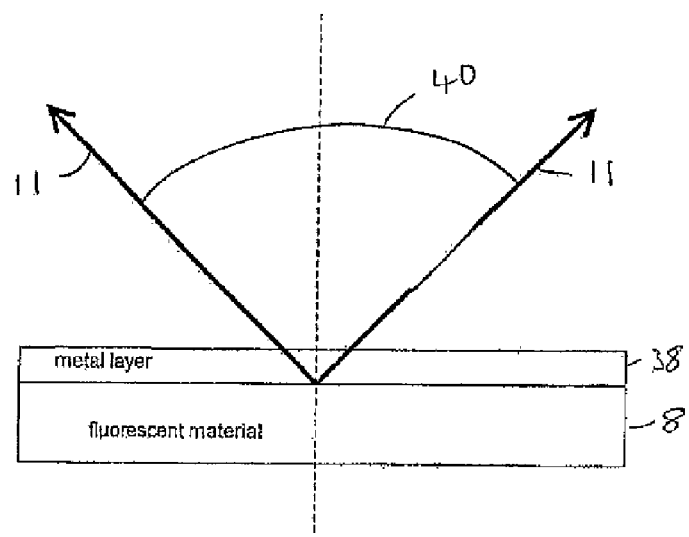
Figure 9:
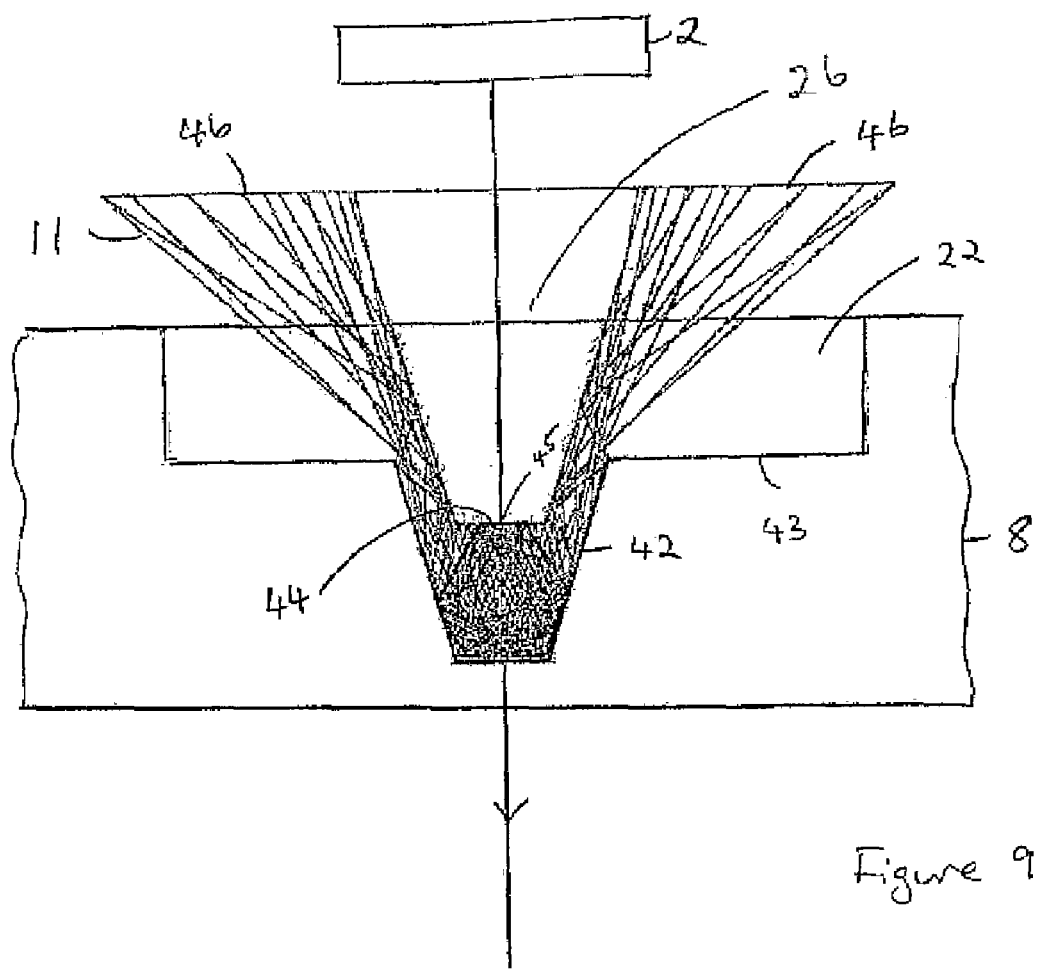
Figure 10:
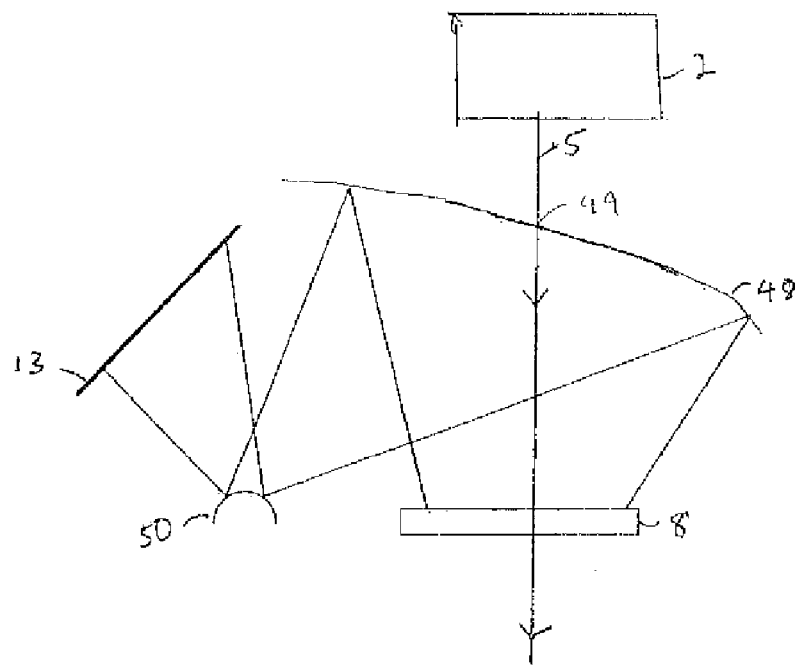
Figure 11:
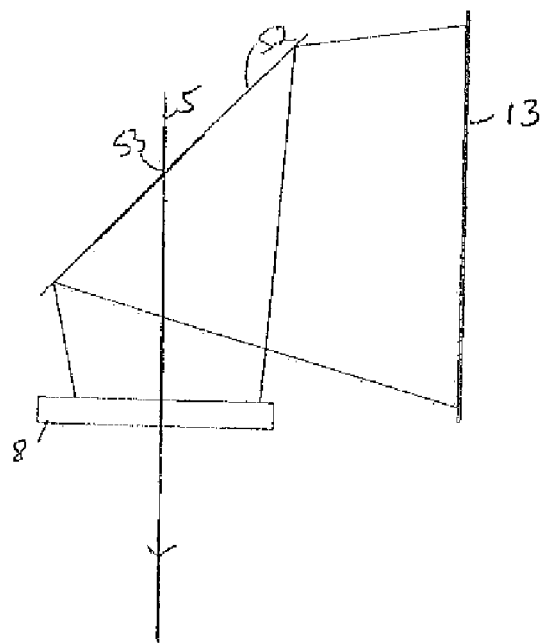
Figure 12:
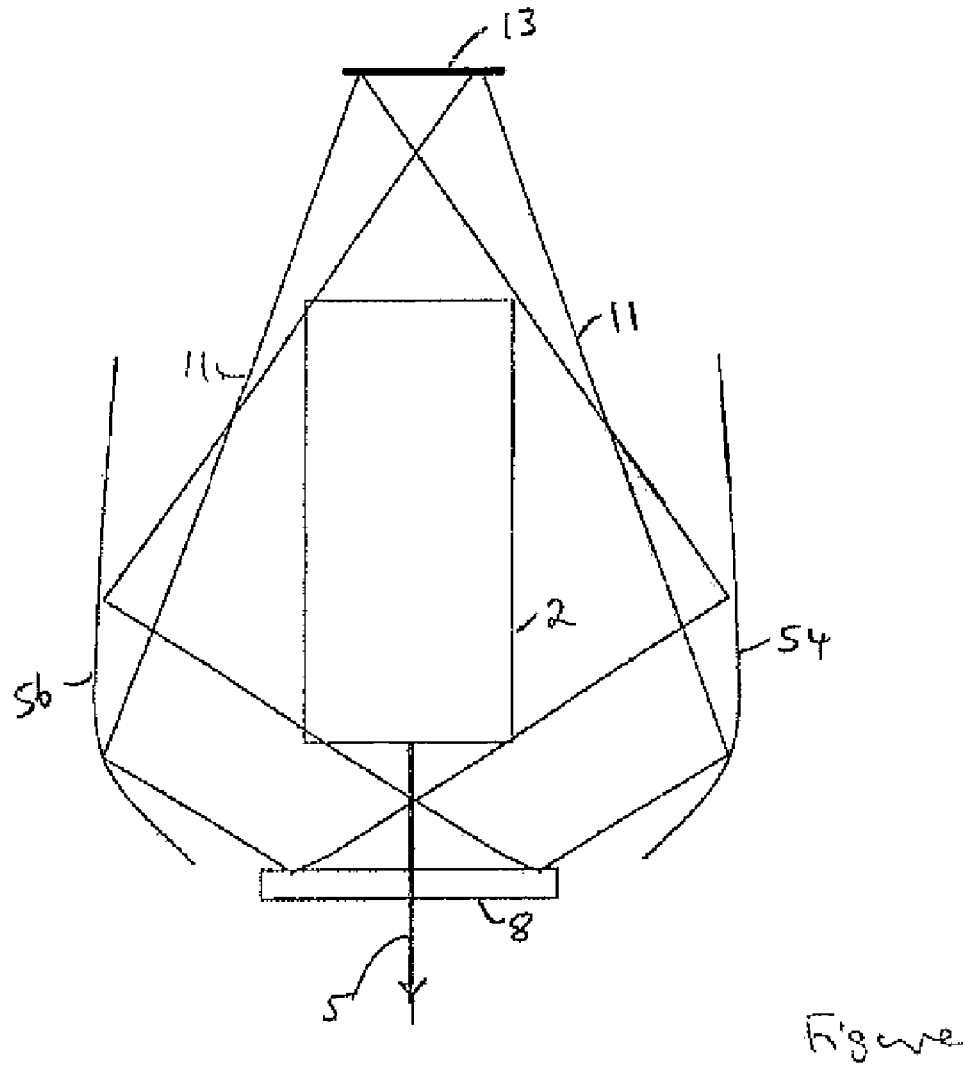

FIG. 5. shows a schematic view of an apparatus according to a fifth embodiment of the invention;

FIG. 6 shows a schematic view of an apparatus according to a sixth embodiment of the invention;

FIG. 7 shows a schematic view of an apparatus according to a seventh embodiment of the invention;

FIG. 8 shows a schematic view of an apparatus according to an eighth embodiment of the invention;

FIG. 9 shows a schematic view of an apparatus according to a ninth embodiment of the invention;

FIG. 10 shows a schematic view of an apparatus according to a tenth embodiment of the invention;

FIG. 11 shows a schematic view of an apparatus according to an eleventh embodiment of the invention, and FIG. 12 shows a schematic view of an apparatus according to a twelfth embodiment of the invention.

Like reference numerals indicate like elements.

The figures are merely schematic views of preferred embodiments according to the invention. In the figures, equal or corresponding parts are referred to by the same reference numbers.

Figure 1:
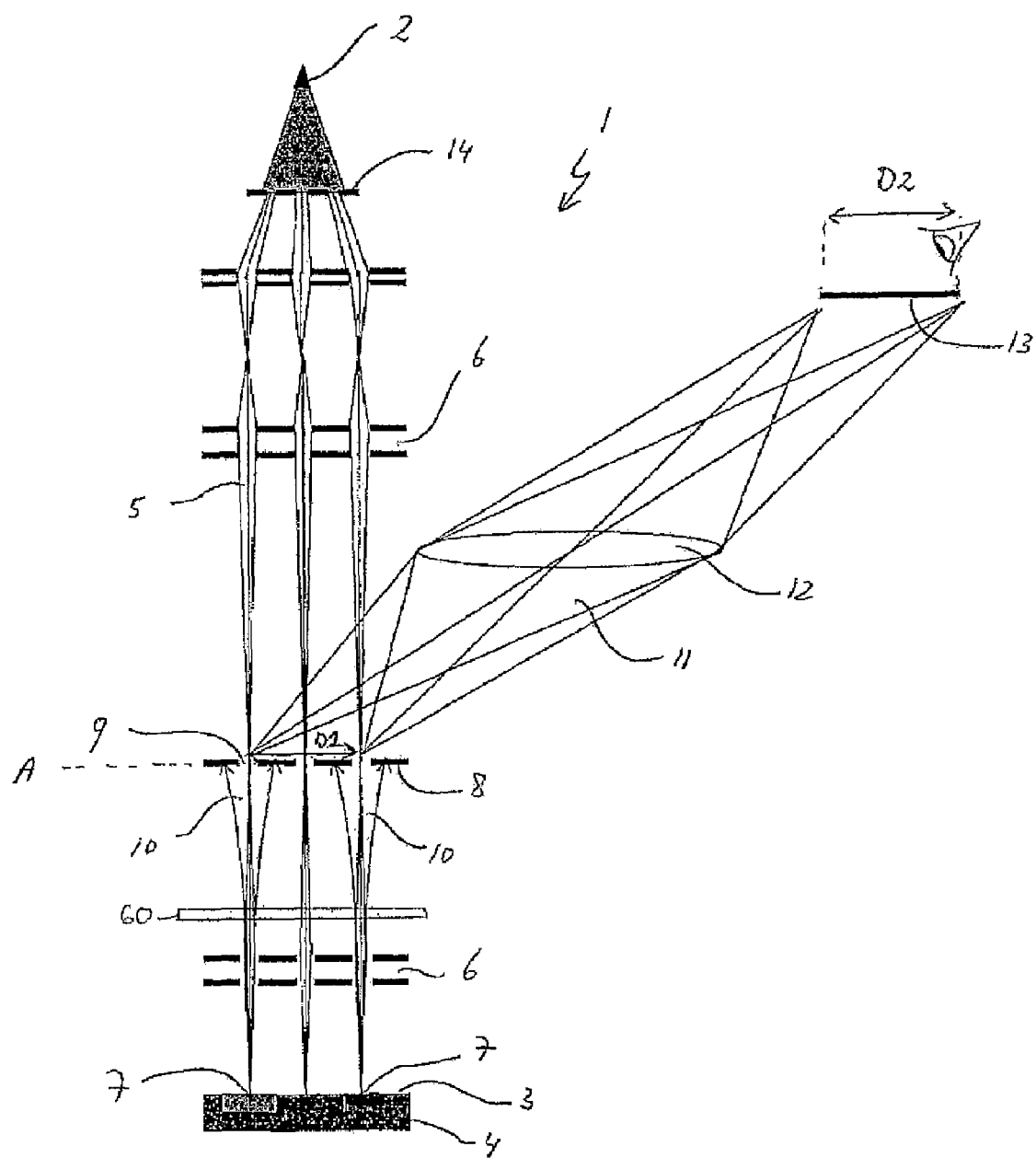

FIG. 1 shows a schematic view of an apparatus 1 for inspecting a specimen surface according to a first embodiment of the invention. The inspection apparatus 1 comprises an electron emitter 2 emitting, in use, a plurality of primary electron beams 5, which are directed towards a surface 3 of a specimen 4 disposed on a table (not shown) of the apparatus 1. Further, the inspection apparatus 1 comprises focussing means embodied as a electron lens system comprising a cascade of lenses 6 to focus the plurality of primary beams 5 onto respective loci 7 on the specimen surface 3. In one of the focus planes A of the plurality of primary beams 5 between the electron emitter 2 and the specimen surface 3, a thin sheet like plate 8 comprising fluorescent material is disposed. The thin sheet 8 comprises apertures 9, so that the primary beams 5 are allowed to pass. By positioning the plate 8 in one of the focus planes A, the dimensions of the apertures may remain minimal, resulting in a maximum surface for converting secondary electron beams into optical beams, as will be explained later. In an alternative embodiment, the plate 8 is disposed beneath a focus plane A. In this way, the overlap of the secondary beams is reduced further or avoided. In a yet further embodiment, the plate 8 is disposed above a focus plane A. In this way, more space is available for additional beam scanning or focussing means.

Upon incidence of the primary beams 5 onto the respective loci 7 on the specimen surface 3 secondary electrons and backscattered electrons forming a plurality of secondary beams 10 originate from the specimen surface 3. The secondary beams 10 are not focussed in the apertures 9 but rather than passing through the apertures 9 they strike the plate 8 which collects the electrons and converts a secondary beam 10 into an optical beam 11 which is focussed by means of an optical lens system 12 onto detection means, embodied as an array of photodetectors 13. In one embodiment, the optical beam is detected with an optical detector. Further, the conversion includes converting at least one of the collected secondary beams at a plane into the optical beam. The optical beam is imaged through free space onto a plane in which the optical detector is located. Further, the optical beam may traverse at least one of the primary beams.

By interpreting the signals detected at the array of photodetectors 13 information from the specimen surface 3 at the loci 7 may be revealed. The inspection apparatus 1 can be used as an inspection tool during manufacturing of chips or after the manufacturing steps have been completed. By adjusting the loci 7 on which the primary beams 5 are focussed, the inspection apparatus can entirely or partly scan the specimen surface 3. Adjustment of the loci 7 can be accomplished by e.g. moving the specimen 4 and/or by repositioning of the primary beams 5.

The lenses 6 of the focussing means can be implemented as micro lenses, comprising conducting aperture plates. These can be manufactured using standard micromachining fabrication techniques. However, the focussing means may also comprise magnetic fields generated by magnet coils.

Preferably, an electrostatic field is generated between the specimen surface 3 and the plate 8 in order to accelerate electrons in the secondary beam 10 and to avoid interference or crosstalk between different secondary beams.

By an appropriate choice of the focal planes of the optical lens system 12, the initial beam dimension D1 of the optical beam 12 is different from the beam dimension at a location where the photodetectors 13 are disposed D2. For example, the initial beam dimension D1 of the optical beam 12 may be smaller than the beam dimension at a location where the photodetectors 13 are disposed D2, thereby improving the quality of the optical beam detection and/or relaxing system requirements for the photodetectors 13. Alternatively, the initial beam diameter may be larger than the beam diameter at a location where the photodetectors are disposed. As an alternative, the optical beam 12 may be guided by means of an optical guide, such as an optical fibre, thereby saving space and relaxing positioning requirements for the photodetectors 13. It is, of course, also possible to combine an optical lens system with an optical fibre structure. The array of photodetectors 13 comprise a CCD camera. However, in an alternative embodiment, the detection means may be implemented in another way, e.g. by using a CMOS image chip with or without active pixel sensors. The detection means may also comprise photodiodes in combination with or without photomultipliers.

In a preferred embodiment, a minimum distance is provided between the primary beams, because it has been found that due to the beam width of the secondary beams 10 interference of secondary beams 10 result in loss of information. In other words, according to an embodiment of the invention, the secondary beams are detected separately from one another, i.e., without any substantial overlap between the secondary beams.

Instead of a fluorescent material, the thin sheet like plate 8 may also comprise other phosphorescent material, or any material having the property that converts an incident electron beam into an optical beam, like a scintillating material, for instance crystal scintillators like YAG, YAP, NaI, and so on, or plastic scintillators, or a fluorescent coating or layer on a transparent substrate, like glass. Instead of using fluorescent material for converting the secondary beam 10 into the optical beam 11, it is also possible to utilize electrochromic films, i.e. films that change optical properties on exposure to electron beam radiation, or current detectors driving LEDs or lasers. In case of the former, the contrast is determined by the difference in electron beam intensity on the electrochromic film, yet the signal can be determined by an intense light source reflecting on the film towards the photodetectors 13. In this manner the problem of detecting a low number of photons for each incident backscattered or secondary electron of the secondary beam 10 is resolved. Electrochromic films are known for usage in smart windows incorporating the modulation of incoming light. Fast devices that allow utilization in LCD-like displays are among the other possibilities.

Instead of positioning the thin plate 8 in one of the focus planes A, it is also possible to position the plate 8 closer to the specimen surface, so that overlap of the secondary beams 10 is reduced or further avoided. It is noted that the plate 8 with the fluorescent material integrates the functionality of collecting the secondary beams 10 and converting a secondary beam 10 into an optical beam 11. As an example, the plate 8 comprises a glass plate supporting a coated fluorescent layer. However, it is also possible to implement the above-mentioned functionalities separately, e.g. by providing an auxiliary structure for improving the properties of receiving the individual secondary electron beams. As an example, this can be implemented by means of strips on the plate 8 which are not transparent for the secondary beams 10 and extend towards the specimen surface 3 in order to separate and collect electrons of adjacent secondary beams 10. Further, the collecting angle of the secondary beams 10 can be increased, reducing crosstalk, either by using small electrodes disposed in between the apertures 9, or by intentionally leaving a part disposed between the apertures electrically isolated. With such an arrangement, the isolated part charges up and the resulting fields act as an electron channel forcing backscattered electrons towards the closest fluorescent site.

If the structure is a plate, the apertures 9 for the primary beams 5 may be drilled or etched. The plate is preferably thick enough to have sufficient mechanical rigidity. Whilst this has repercussions on the minimal diameter, and consequently the 'detector spacing', of the apertures 9, it has been found that the rigidity of the plate may be improved by using a segmented plate, which is relatively thin and may be embedded in a grid for extra support. As an alternative, the plate 8 may have other configurations, e.g. it may be configured as a curved surface. For example, the plate may be of a glass material, or glass with a fluorescent layer or a fluorescent material.

The inspection apparatus, shown in FIG. 1, comprises a single electron emitter illuminating an aperture array 14, thus emitting the plurality of primary electron beams. An alternative construction may be formed by providing an array of electron emitters.

In one embodiment, a micro channel plate (MCP) 60 is provided. The micro channel plate 60 may be positioned between the specimen 4 and the converting means 8, such as the fluorescent screen. The micro channel plate 60 is constructed such that the primary beam(s) 5 are allowed to pass, in order to increase the current in the secondary beam(s) 10 before conversion to an optical beam 11. A micro channel plate may also be provided in the embodiments shown in FIGS. 2-12. In particular, a micro channel plate 60 may be provided in the embodiment shown in FIG. 4, in which case, the micro channel plate 60 is provide to increase the current in the secondary beam(s) 10 before conversion to an electronic signal.

Figure 2:
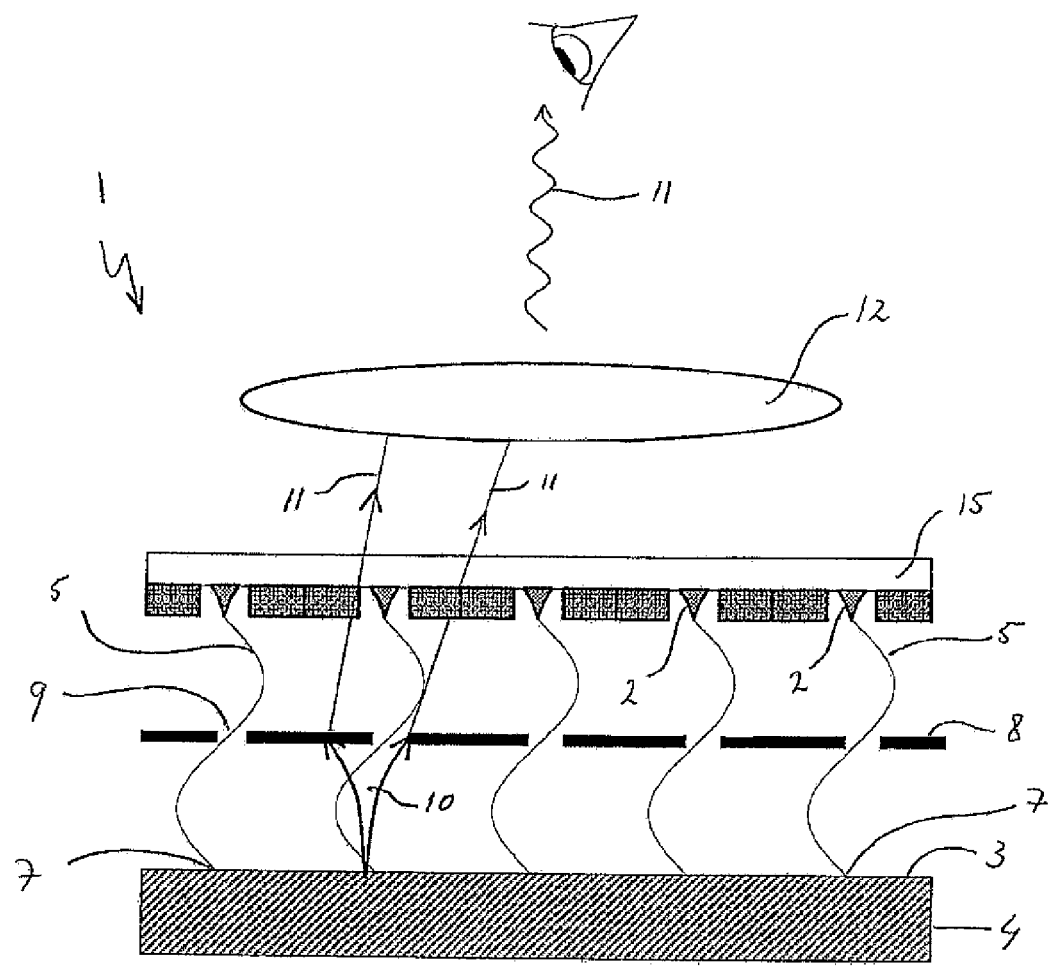
FIG. 2 shows a schematic view of an apparatus according to a second embodiment of the invention.

FIG. 2 shows a schematic view of an inspection apparatus according to a second embodiment of the invention. The inspection apparatus 1 comprises an array of electron emitters 2 emitting a plurality of primary electron beams 5 which are focussed by means of a substantially uniform magnetic field. The plurality of primary electron beams 5 propagate through apertures 9 in a thin sheet like plate 8 comprising fluorescent material. Secondary electron beams 10 are collected and converted to optical beams 11 which propagate in the direction of the array of electron emitters 2 and traverse through an optically transparent layer 15 disposed above the emitters 2. Further, the optical beams 11 are focussed on detection means, such as a CCD camera, by means of an optical lens system 12. The detection means may also comprise other CCD sensors and/or a CMOS active pixel sensor, and/or a photodiode array.

Figure 3:
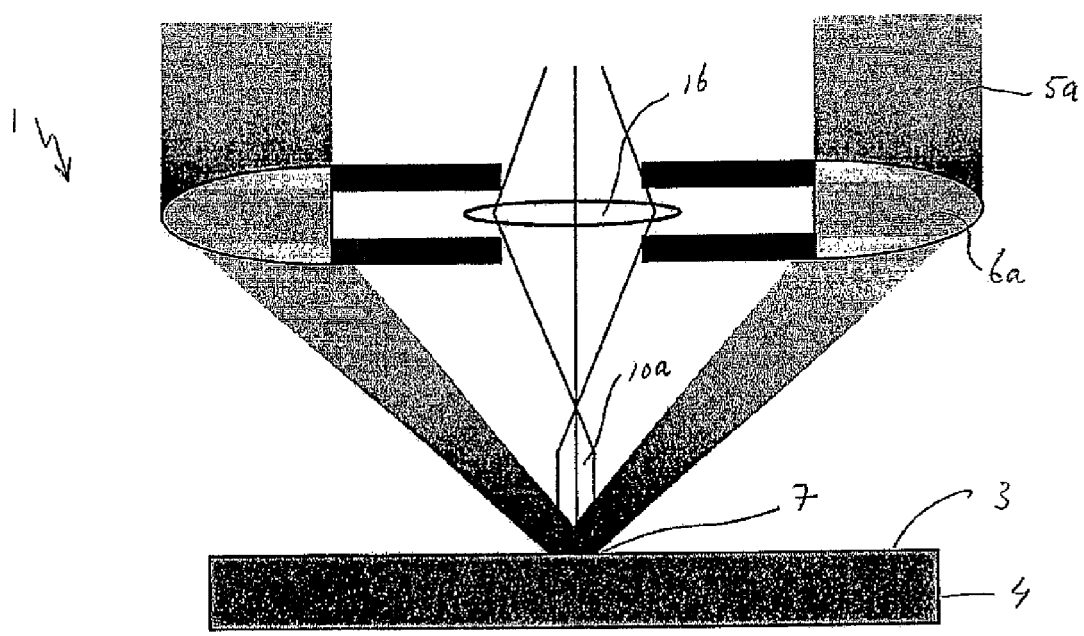
FIG. 3 shows a schematic view of an apparatus according to a third embodiment of the invention.

FIG. 3 shows a schematic view of an inspection apparatus according to a third embodiment of the invention. The inspection apparatus 1 comprises an emitter (not shown) emitting a plurality of primary photon beams 5a directed towards a specimen surface 3. An optical lens system 6a focuses the primary optical beams 5a onto loci 7 on the specimen surface 3. In contrast to the preceding embodiments according to the invention, the primary beam 5a is relatively broad. Upon incidence of the primary beam 5a, a secondary, photoinduced electron beam 10a is emitted which contains spatial information of the surface being impinged by the relatively broad primary beam 5a and which passes through an electronic lens 16 arranged in the centre of the optical lens system 6a. Again, as in the previous embodiments, the secondary electron beam 10a is collected and converted to an optical beam, and subsequently detected by photodetectors (not shown). The information relative to the specimen surface 3 is obtained by processing and imaging the spatial distribution of the detected optical beam, as the optical beams contains spatial information of the surface structure in the relatively broad loci 7.

Figure 4:
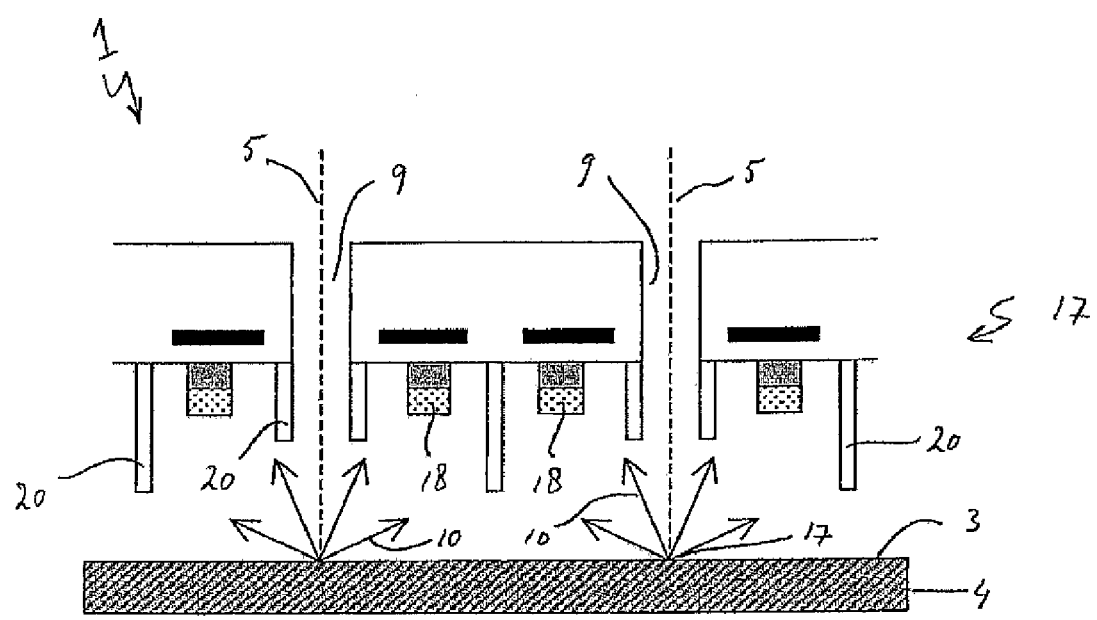
FIG. 4 shows a schematic view of an apparatus according to a fourth embodiment of the invention.

FIG. 4 shows a schematic view of an inspection apparatus according to a fourth embodiment of the invention. In the inspection apparatus 1 the emission process of the plurality of primary beams 5 as well as lens systems are identical to the process and lens systems described under reference to FIG. 1. However, instead of the thin sheet like plate 8, a micro electro mechanical system (MEMS) 17 is disposed between the emitter and the specimen surface 3. The MEMS 17 comprises an array of diodes 18 interspersed with apertures 9 to allow transmittance of the primary electron beams 5. A secondary electron beam 10 is detected by a diode 18. Each detecting area 19 in which a diode 18 is disposed is preferably equipped with electrodes 20 to increase the collecting angle by electrostatic focussing. These electrodes 20 also serve to prevent crosstalk between backscattered beams from neighbouring detecting areas 19. Additionally, there is space for embedded electronics to perform some 'on-detector' arithmetic data processing. For instance, addition and subtraction of symmetrically placed diodes 18 gives respectively compositional and topological information; these operations can be implemented on the MEMS 17. For data transport to peripheral instruments the MEMS advantageously might be implemented with a CCD-grid like array, so that an order of a million diodes may be read separately.

In the embodiment described under reference to FIG. 4, the step of detecting the optical beam is accomplished at a location within a volume being traversed by the plurality of primary beams, as the diodes 18 on the MEMS 17 might convert the secondary beam into an optical beam and subsequently detect the optical beam. In this process, detection is carried out near the surface 3 of the specimen 4, thereby increasing the quality of the measurement detection of the inspection apparatus 1. In essence, the design of the apparatus may be simplified due to the omission of detection instruments outside the volume enclosing the space being traversed by the plurality of primary beams. It is noted, however, that it is also possible to convert the collected secondary beams directly to an electronic signal without generating an optical signal. In particular, a method of inspecting a specimen surface may comprise the steps of generating a plurality of primary beams directed towards the specimen surface, focussing the plurality of primary beams onto respective loci on the specimen surface, collecting a plurality of secondary beams of charged particles originating from the specimen surface upon incidence of the primary beams, and converting at least one of the collected secondary beams directly into an electronic signal.

As described above, a high throughput, high resolution semiconductor inspection using parallel electron beam microscopy makes use of a converting means 8, for example, a fluorescent plate 8 that is adapted on the one hand to allow passage of one or more primary beams 5, and on the other hand generates photons 11 upon incidence of secondary electrons 10, emitted from the inspected sample 3. The photons 11 emanating from the fluorescent plate 8 are collected using an optical system 12 and detected with a photon detection system 13. The fluorescent plate preferably emits many photons per incident electron, and further, preferably, has a short fluorescence decay time. Preferred materials, including a YAP scintillator, satisfy these criteria. It has been found, however, that such materials, emit photons into a half sphere. It has further been found that the optical system 12 used to image the emitted photons on the photon detection system does not effectively collect the entire emission solid angle because the electron optical system including the emitter for emitting the one or more primary beams, blocks a large part of the solid angle. Thus, it is further object of the present invention to increase the number of photons per incident electron detected by the detection means 13. Since, it has been found that for the signal-to-noise performance of the inspection tool, it is necessary to collect a substantial number of photons per incident electron from the converting means, for example, the fluorescent plate, onto the photon detection system. However, due to a low typical yield of the fluorescent plate, the demands on the photon collection system 12 become difficult to deal with, due to the loss of photons outside the collectible light cone. It is thus, a further object of the present invention to improve the proportion of photons arriving at the detection means. This object is addressed, in particular, by the sixth to ninth aspects of the present invention. By providing a directing means for directing the optical beam towards a detection means, the proportion of photons reaching the detection means is improved, thus, improving the signal to noise ratio. Further, the object may be addressed by directing the light output such, that the photon emission cone is no longer, or to a lesser extent, obscured by the electron optics. Particular embodiments of the invention addressing this object are shown and described with reference to FIGS. 5 to 12.

FIG. 5. shows a schematic view of an apparatus according to a fifth embodiment of the invention. FIG. 5 shows a converting means 8, for example, a fluorescent plate-like structure including a fluorescent material, as described above. In the embodiments shown in FIGS. 5-12, a directing means 22 directs the light output by the converting means 8 in a predetermined direction. In particular, the directing means may be arranged to change the direction in a predetermined manner in which the optical beam 11 propagates. In the embodiments shown in FIG. 5-9, the directing means 22 is integrated in the converting means. Alternatively, the directing means 22 is provided separately from the converting means, as shown in the embodiments depicted in FIGS. 10-12.

In FIG. 5, the fluorescent material 8 is provided with holes 24 to allow the one or more primary beams 5 to pass. The directing means 22 comprises one or more cavities. The cavities are relatively small. The cavities may have reflective walls 25 formed in the fluorescent material. Per cavity, one relatively small opening 26 is provided. The opening is dimensioned such that the optical beam is emitted from the cavity through the opening 26. The light escapes through the opening. Although the photons may still exit from the cavities 22 at all possible angles, they will only exit through the small opening.

FIG. 6 shows a schematic view of an apparatus according to a sixth embodiment of the invention. It has been found that the provision of openings 26 through which the light can exit the cavities 22 allows the placement of an optical microlens array 28 on the cavities. Thus, the directing means 22, 28 may also comprise a microlens array 28 comprising a plurality of microlenses, disposed on the fluorescent material 8. The microlens array 28 is provided with holes 30 to allow the one or more primary beams 5 to pass. The microlens array 22 is arranged so that the microlenses magnify the holes 26 in the cavities 22. For example, the microlenses are substantially aligned with respect to the cavities. In this way, the opening angle 32 of the cavities 22 from which the optical beam 11 is emitted is limited. Thus, in this way, all light emitted from the cavity 22 can be directed directly on to the optical system 12, including, for example, a lens, which further focuses the optical beam 11 onto the detection means 13, as described with reference to FIG. 1. Even in the absence of reflective cavities with a small opening, microlens array 28 may be used to reduce the opening angle while maintaining the same amount of light.

FIG. 7 shows a schematic view of an apparatus according to a seventh embodiment of the invention. As an alternative, or in addition to the microlens array 28, in a further seventh embodiment as depicted in FIG. 7, the directing means may further comprise one or more concave mirrors 34 comprising a relatively small opening 36. In one embodiment, the mirror 34 is a spherical mirror. The mirror 34 is disposed above the one or more cavities 22, respectively. In this way, the opening angle 32 of the optical beam 11 is determined by the opening 36 in the mirror 34. The mirror is arranged so that the light is reflected back into the volume between the mirror and the fluorescent material 8. In this way, light can only leave the converting means 8 under a specified opening angle determined by the opening in the spherical mirror. The smaller the opening the smaller the opening angle. With a reduced opening angle an increased directionality of the optical beam 11 is achieved.

FIG. 8 shows a schematic view of an apparatus according to an eighth embodiment of the invention. In an eighth embodiment, the directing means to direct the light output from a fluorescent material, uses plasmon coupled scintillation. In this embodiment, a metal film 38 is deposited on a layer of fluorescent material 8. In particular, the metal film 38, which determines the angle 40 at which the optical beam 11 is emitted from the converting means 8. The angle 40 at which the optical beam 11 is emitted is determined by phonon coupling due to the thickness of the metal layer. Preferably, the metal film is very thin, for example, in the region of 30 nanometers and is deposited on a thin layer of fluorescent material, for example, in the region of 200 nanometers. It has been found that this arrangement results in a very sharp peak in the angular density of the emitted light at an angle that can be controlled by varying the thickness of the metal film. In this way, a very large proportion of the light can be aimed from the converting means directly on to a lens 12, as shown in FIGS. 1 and 6.

FIG. 9 shows a schematic view of an apparatus according to a ninth embodiment of the invention. In a ninth embodiment, the directing means 22, 42, 44 is arranged to direct the optical beam in an annular emission cone 46. In the ninth embodiment, the directing means comprises cone-shaped cavities 42. The cone shaped cavities 42 preferably have highly reflective walls 43 formed in the fluorescent material 8. Further, in the cone-shaped cavities, a truncated cone shaped reflective protrusion 44 is provided extending into the cavity 42. The protrusion 44 may be provided with an opening 45 to allow a primary beam 5 to pass. In this way, the light will be emitted in an annular emission cone so that the electron emitter 2, including an electron optical system, for emitting the one or more primary beam 5, does not obscure the light path traveled by the optical beam 11.

In the tenth to twelfth embodiments, the directing means 48, 50, 52, 54, 56 is disposed at a remote location from the converting means 8. In particular, the directing means 48, 50, 52, 54, 56 is disposed at a location between the converting means 8 and the detection means 13.

In the embodiments shown, the directing means comprise mirrors. In addition, however, the directing means may comprise prisms, lenses and other means for changing the direction in which the optical beam 11 propagates.

FIG. 10 shows a schematic view of an apparatus according to a tenth embodiment of the invention. In the tenth embodiment, the directing means 48 comprises a curved concave mirror for directing the light beam 11 towards the detection system 13. In the embodiment shown, the concave mirror 48 is disposed above the converting means. Further, one or more openings 49 are provided in the concave mirror 48 to allow the one or more primary beams 5 to pass. The mirror is located relatively close to the converting means 8. In this way, the mirror reflects almost all of the light in a convenient direction so that the electron emitter 2, including the electron optics system, does not obscure the light path. The directing means may further comprise a convex secondary mirror 50 which reflects the light reflected from the concave mirror 48 to the detection means 13. The concave mirror 48 and the convex secondary mirror 50 form a Schwarzschild optical system.

FIG. 11 shows a schematic view of an apparatus according to an eleventh embodiment of the invention. In the eleventh embodiment, the directing means comprises a mirror 52. In the embodiment shown, the mirror 52 is planar. The mirror is provided with one or more openings 53 to allow the one or more primary beams 5 to pass. The mirror 52 directs the light output from the converting means 8 to the detection means 13.

FIG. 12 shows a schematic view of an apparatus according to a twelfth embodiment of the invention. In the twelfth embodiment, the directing means 54, 56 is disposed around the emitter 2 for emitting one or more primary beams 5. The mirror 54, 56 is preferably a cylindrical mirror. In this way, although the emitter 2 may partially obscure the beam, the remaining, substantial part of the cone is efficiently directed towards the detection means.

In the embodiments shown in FIGS. 5-12, one primary beam 5 is shown. As shown in FIG. 1, for example, in the embodiments shown in FIGS. 5-12, there may also be a plurality of primary beams. From the embodiments shown in FIGS. 5-12, it is seen that the provision of a directing means increases the design flexibility of the inspection apparatus, since the detection means may be disposed at a variety of locations depending on the particular directing means. For example, in the embodiment shown, in the FIG. 12, the provision of a mirror 54, 56 disposed around the emitter 2, the detection means can be disposed behind the emitter 2. Further, the directing means can be selected in accordance with the type and dimensions of the detection means. In this way, the design freedom of the apparatus is increased.

The invention is not restricted to the embodiments described herein. It will be understood that many variants are possible. In the described methods and apparatuses, the primary electron beams are arranged in such a way that the plurality of primary beams propagate in a substantially parallel direction, so that mutual interaction of the primary beams is avoided and each of the primary beams is focussed onto a single locus on the specimen surface. However, the plurality of primary beams can also be tilted, such that two or more primary beams are focussed onto a single locus, for example, to enhance specific features of the specimen being inspected.

Further variants are considered to lie within the scope of the invention as formulated in the following claims.

The invention claimed is:

1. Method of inspecting a specimen surface, comprising the steps of
    generating a plurality of primary beams directed towards the specimen surface;
    focussing the plurality of primary beams onto respective loci on the specimen surface;
    collecting a plurality of secondary beams of charged particles originating from the specimen surface upon incidence of the primary beams;
    converting at least one of the collected secondary beams at a plane into an optical beam, the optical beam being imaged through free space, the optical beam traversing at least one of the primary beams onto a plane in which an optical detector is located; and
    detecting the optical beam with the optical detector.

2. Method according to claim 1, wherein the step of converting the collected secondary beam into the optical beam is accomplished by means of fluorescent material.

3. Method according to claim 2, comprising disposing the fluorescent material between an emitter of the plurality of primary beams and the specimen surface, wherein the fluorescent material is arranged to allow the primary beams to pass.

4. Method according to claim 1, wherein the step of detecting the optical beam is accomplished in a detection region outside of a volume enclosing the space being traversed by the plurality of primary beams.

5. Method according to claim 1, comprising the step of focussing the optical beam onto a detection system in the detection region.

6. Method according to claim 5, wherein the initial beam diameter of the optical beam is different from the beam diameter at a location where the detection system is disposed.

7. Method of inspecting a specimen surface, comprising the steps of:
    generating a plurality of primary beams directed towards the specimen surface;
    focussing the plurality of primary beams onto respective loci on the specimen surface;
    collecting a plurality of secondary beams of charged particles originating from the specimen surface upon incidence of the primary beams;

converting at least one of the collected secondary beams into an optical beam; and detecting the optical beam at a location within a volume being traversed by the plurality of primary beams.

8. Method according to claim 7, wherein the step of detecting the optical beams is accomplished by means of a micro electro mechanical system.

9. Method of inspecting a specimen surface, comprising the steps of:
generating a plurality of primary beams directed towards the specimen surface;
focussing the plurality of primary beams onto respective loci on the specimen surface;
collecting a plurality of secondary beams of charged particles originating from the specimen surface upon incidence of the primary beams;
converting at least one of the collected secondary beams into an optical beam by means of at least one of a electrochromic material and one or more current detectors driving at least one of a light emitting diode (LED) and a laser; and
detecting the optical beam.

10. Method according to claim 1, wherein the step of detecting the optical beam is accomplished by an optical waveguide arranged to direct the optical beam to an optical detector.

11. Method according to claim 1, wherein the primary beams are relatively broad beams compared to the secondary beams and the secondary beams include spatial information of the surface being impinged by the relatively broad primary beams.

12. Apparatus for inspecting a specimen surface, comprising
at least one emitter arranged to emit a plurality of primary beams directed towards the specimen surface;
focussing means arranged to focus the plurality of primary beams onto respective loci on the specimen surface;
collecting means for collecting a plurality of secondary beams of charged particles originating from the specimen surface upon incidence of the primary beams;
converting means for converting at least one of the collected secondary beams into an optical beam, the converting means being configured to convert at least one of the collected secondary beams at a plane into the optical beam; and
detection means for detecting the optical beam, the detection means including an optical detector for detecting the optical beam;
the optical beam being imaged through free space, the optical beam traversing at least one of the primary beams onto a plane in which the optical detection means is located.

13. Apparatus according to, claim 12, wherein the converting means comprises fluorescent material.

14. Apparatus according to claim 13, wherein the fluorescent material is disposed on a screen.

15. Apparatus according to claim 14, wherein the fluorescent screen is disposed between the at least one emitter and the specimen surface, and is constructed such that the primary beams are allowed to pass.

16. Apparatus according to claim 12, wherein the collecting means and the converting means are integrated.

17. Apparatus according to claim 12, wherein the detection means are located outside of a volume enclosing the space being traversed by the plurality of primary beams.

18. Apparatus according to claim 12, further comprising optical focussing means for focussing the optical beams to the detection means.

19. Apparatus according to claim 12, further comprising a micro electro mechanical system for detecting the optical beams at a location within a volume being traversed by the plurality of primary beams.

20. Apparatus according to claim 12, wherein a minimum distance is provided between the primary beams, so that any substantial overlap between the secondary beams is avoided.

21. Apparatus according to claim 12, wherein the primary beams are relatively broad beams compared to the secondary beams and the secondary beams include spatial information of the surface being impinged by the relatively broad primary beams.

22. Apparatus for inspecting a specimen surface, comprising:
one or more emitters arranged to emit one or more primary beams directed towards the specimen surface;
collecting means for collecting one or more secondary beams of charged particles originating from the specimen surface upon incidence of the one or more primary beams;
converting means for converting at least one of the collected secondary beams into an optical beam; directing means for directing the optical beam towards a detection means, the directing means being integrated in the converting means, the directing means including one or more cavities having reflective walls in the fluorescent material; and
the detection means for detecting the optical beam.

23. An apparatus according to claim 22, wherein the directing means directs the light output from the converting means in a predetermined direction.

24. An apparatus according to claim 22, wherein the directing means is arranged to change the direction in which the optical beam propagates in a predetermined manner.

25. An apparatus according to claim 22, wherein the converting means comprises a fluorescent material disposed in the form of a plate like structure.

26. An apparatus according to claim 22, wherein the cavities comprise a relatively small opening dimensioned so that the optical beam is emitted from the cavity through the opening.

27. An apparatus for inspecting a specimen surface, comprising:
one or more emitters arranged to emit one or more primary beams directed towards the specimen surface;
collecting means for collecting one or more secondary beams of charged particles originating from the specimen surface upon incidence of the one or more primary beams;
converting means for converting at least one of the collected secondary beams into an optical beam; directing means for directing the optical beam towards a detection means, the directing means including a microlens array having a plurality of microlenses, disposed on the fluorescent material, so that the microlenses are arranged to reduce the opening angle of the optical beamlets while maintaining the same amount of light; and
the detection means for detecting the optical beam.

28. An apparatus according to claim 27, wherein:
the directing means includes one or more cavities having reflective walls in the fluorescent material; and
the microlenses are substantially aligned with respect to the cavities, respectively.

29. An apparatus for inspecting a specimen surface, comprising:
one or more emitters arranged to emit one or more primary beams directed towards the specimen surface;
collecting means for collecting one or more secondary beams of charged particles originating from the specimen surface upon incidence of the one or more primary beams;
converting means for converting at least one of the collected secondary beams into an optical beam; directing means for directing the optical beam towards a detection means, the directing means further including one or more concave mirrors having a relatively small opening, disposed above the one or more cavities, respectively, so that the opening angle of the optical beam is determined by the opening in the mirror; and
the detection means for detecting the optical beam.

30. An apparatus according to claim 29, wherein the one or more concave mirrors is spherical.

31. An apparatus for inspecting a specimen surface, comprising:
one or more emitters arranged to emit one or more primary beams directed towards the specimen surface;
collecting means for collecting one or more secondary beams of charged particles originating from the specimen surface upon incidence of the one or more primary beams;
converting means for converting at least one of the collected secondary beams into an optical beam; directing means for directing the optical beam towards a detection means, the directing means using plasmon coupled scintillation to direct light output from the converting means; and
the detection means for detecting the optical beam.

32. An apparatus for inspecting a specimen surface, comprising:
one or more emitters arranged to emit one or more primary beams directed towards the specimen surface;
collecting means for collecting one or more secondary beams of charged particles originating from the specimen surface upon incidence of the one or more primary beams;
converting means for converting at least one of the collected secondary beams into an optical beam; directing means for directing the optical beam towards a detection means, the directing means including a metal film and the converting means including a layer of fluorescent material, the metal film being deposited on the fluorescent material; and
the detection means for detecting the optical beam.

33. An apparatus according to claim 32, wherein the metal film has a thickness, the thickness determining the angle at which the optical beam is emitted from the converting means.

34. An apparatus according to claim 33, wherein the angle at which the optical beam is emitted is determined by phonon coupling due to the thickness of the metal layer.

35. An apparatus according to claim 22, wherein the directing means is arranged to direct the optical beam in an annular emission cone.

36. An apparatus according to claim 22 wherein the cavities are cone-shaped.

37. An apparatus according to claim 22, wherein the one or more cavity includes a truncated cone shaped reflective protrusion extending into the cavity.

38. An apparatus according to claim 37, wherein the protrusion is provided with an opening to allow a primary beam to pass.

39. An apparatus according to claim 22, wherein the directing means is disposed at a location between the converting means and the detection means.

40. An apparatus according to claim 39, wherein the directing means comprises at least one of a lens, a mirror and a prism.

41. An apparatus according to claim 40, wherein the directing means comprises a curved concave mirror disposed above the converting means.

42. An apparatus according to claim 41, wherein the directing means comprises a Schwarzschild optical system.

43. An apparatus according to claim 39, wherein the directing means is provided with one or more openings to allow the one or more primary beams to pass, respectively.

44. An apparatus for inspecting a specimen surface, comprising:
one or more emitters arranged to emit one or more primary beams directed towards the specimen surface;
collecting means for collecting one or more secondary beams of charged particles originating from the specimen surface upon incidence of the one or more primary beams;
converting means for converting at least one of the collected secondary beams into an optical beam; directing means for directing the optical beam towards a detection means, the directing means is disposed around the one or more emitter; and
the detection means for detecting the optical beam.

45. A fluorescent plate for use in an inspection apparatus according to claim 25.

46. A fluorescent plate and a directing means for use in an inspection apparatus according to claim 25.

47. An apparatus according to claim 12, further comprising a micro channel plate (MCP) positioned between the specimen and the converting means, the micro channel plate being constructed such that the primary beam(s) are allowed to pass, in order to increase the current in the secondary beam(s) before conversion to an optical beam or electronic signal.

* * * * *